(12) United States Patent
Young et al.

(10) Patent No.: US 8,180,652 B2
(45) Date of Patent: May 15, 2012

(54) REMOTE HEALTHCARE METHOD FOR MEASURING PHYSIOLOGICAL PARAMETER AND REPORTING SELF-PERCEIVED HEALTH STATUS

(75) Inventors: Shuenn-Tsong Young, Hsinchu County (TW); Chung-Wang Lee, Hsinchu County (TW); Chang-Yu Liu, Hsinchu County (TW)

(73) Assignee: Aescu Technology Inc., Hsinchu County (TW)

( * ) Notice: Subject to any disclaimer, the term of this patent is extended or adjusted under 35 U.S.C. 154(b) by 175 days.

(21) Appl. No.: 12/801,988

(22) Filed: Jul. 7, 2010

(65) Prior Publication Data

US 2011/0046971 A1    Feb. 24, 2011

(30) Foreign Application Priority Data

Aug. 19, 2009   (TW) .............................. 98127820 A

(51) Int. Cl.
*G06Q 10/00*   (2012.01)
(52) U.S. Cl. ............. 705/2; 340/9.1; 600/300; 600/508; 600/509; 604/67; 607/2; 607/60; 709/219
(58) Field of Classification Search .................. 705/2, 3; 340/9.1; 600/300, 508, 509; 604/67; 607/2, 607/60; 709/219
See application file for complete search history.

(56) References Cited

U.S. PATENT DOCUMENTS

| | | | |
|---|---|---|---|
| 5,986,568 A * | 11/1999 | Suzuki et al. ................. | 340/9.1 |
| 6,336,903 B1 * | 1/2002 | Bardy ........................... | 600/508 |
| 6,699,188 B2 * | 3/2004 | Wessel ......................... | 600/300 |
| 7,181,505 B2 * | 2/2007 | Haller et al. .................. | 709/219 |
| 7,577,475 B2 * | 8/2009 | Cosentino et al. ............ | 600/509 |
| 7,729,760 B2 * | 6/2010 | Patel et al. ...................... | 607/2 |
| 2005/0277872 A1 * | 12/2005 | Colby et al. ...................... | 604/67 |
| 2008/0269569 A1 * | 10/2008 | Kukla et al. ................... | 600/300 |
| 2009/0149719 A1 * | 6/2009 | Wariar et al. ................. | 600/300 |
| 2009/0228073 A1 * | 9/2009 | Scholten ......................... | 607/60 |

OTHER PUBLICATIONS

Google patents search.*
Google patents search_2.*
Dialog search.*

* cited by examiner

*Primary Examiner* — Dilek B Cobanoglu
(74) *Attorney, Agent, or Firm* — Bacon & Thomas, PLLC

(57) ABSTRACT

A remote healthcare method is applied to a healthcare server and includes the steps of receiving detected information from a physiological parameter detecting instrument, reading a patient identification code and a physiological parameter from the detected information, reading an identification datum and a medical history datum matched with the patient identification code from a history database according to the identification code, reading a disease matched with the disease classification code and a corresponding pathological symptom from the disease database according to at least one disease classification code in the medical history data, screening a corresponding matched pathological symptom from the pathological symptoms according to the read physiological parameter to create a self-perceived list, transmitting the self-perceived list to the physiological parameter detecting instrument, and waiting for a receipt of the selected option of the pathological symptom for determining an appropriate medical dosage or medical tool.

20 Claims, 5 Drawing Sheets

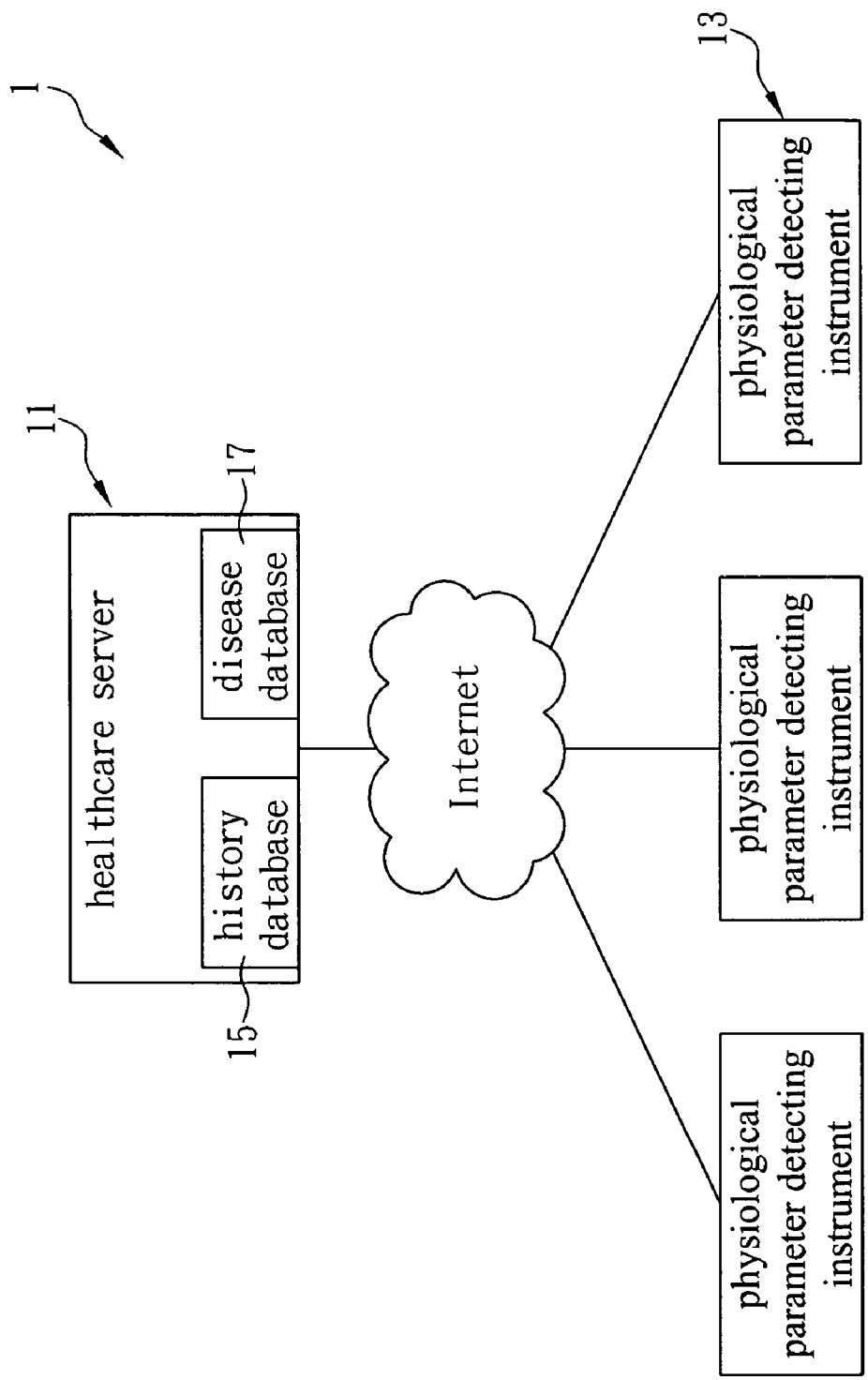

| 1511 | | 1513 | | 1515 |
|---|---|---|---|---|
| 001 | John | 30 years old | Taipei city | A, B |
| 002 | Peter | 16 years old | Kaohsiung | C |
| 003 | Mary | 78 years old | Yilan | B, C, D |
| 004 | Lisa | 66 years old | Miauli | A, D |
| ... | ... | ... | ... | ... |

| 1711 | 1713 | 1715 |
|---|---|---|
| A | Heart disease | Dizziness, heart throb, breathing difficulty, chest pain ..... |
| B | Kidney disease | Edema, polyuria, backache ..... |
| C | Diabetes | Polyuria, thirty, fatigue ..... |
| D | Chronic liver disease | Fatigue, loss of appetite, nausea ..... |
| ... | ... | ... |

Enter your symptoms

Dizziness

Heart throb

Breathing difficulty

None

Confirm

Return

REMOTE HEALTHCARE METHOD FOR MEASURING PHYSIOLOGICAL PARAMETER AND REPORTING SELF-PERCEIVED HEALTH STATUS

FIELD OF THE INVENTION

The present invention relates to a remote healthcare method, in particular to a remote healthcare method that creates a self-perceived list containing an appropriate number of options of pathological symptoms according to a patient's past medical history and current physiological parameter, and the self-perceived list is provided for the patient to select the options.

BACKGROUND OF THE INVENTION

As medical technologies advance, our average life becomes increasingly longer, and ageing population tends to be increased in a substantially large percentage. To cope with the medical technology and social security system caused by the ageing population, medical teams, academic circles and related manufacturers conduct research and development, and promote remote homecare and medical service to establish a remote healthcare network, so as to overcome the healthcare problems of elderly people and improve the situation of having insufficient medical resources in remote areas.

In general, the so-called "remote homecare" or "remote medical service" installs a physiological parameter detecting instrument on a patient's body for detecting the patient's physiological signal (including blood pressure, heartbeat, blood sugar level and related information) and transmitting the same to a remote healthcare center via the Internet or a telephone network, such that the patient's family or an attending doctor can know about the patient's physiological conditions, and compile and save the patient's physiological parameter history data to determine the patient's condition in order to provide timely homecare or medical service when the patient is unwell or in a critical condition. An immediate handling method can be informed through the physiological parameter detecting instrument, or an immediate notice or advice can be delivered to a medical professional for medical helps. Thus, the remote homecare or remote medical service can overcome the limitations of time and space by shifting the medical treatment activities originally conducted in hospitals or clinics to the patient's home, and also can improve the patient's safety as well.

To achieve the aforementioned purposes and further promote the remote homecare or remote medical service, related manufacturers, hospitals and clinics continuously conduct researches for improvements and look for feasible solutions. However, the remote homecare or remote medical service still has many problems till now. Firstly, most physiological parameter detecting instruments can just return a patient's physiological parameters directly, so that the medical professionals of the healthcare center can base on the physiological parameter for analyses, or combine several physiological parameters to determine the patient's physiological conditions. Therefore, the quality and professionalism of the medical professionals are important factors for determining a patient's current physical condition accurately. In addition, the numeric value of a physiological parameter varies with the patient's mood, environment, weather or daily activity. If the numeric value of the patient's physiological parameter has not exceeded a critical value predetermined by medical professionals, then the medical professional generally will assume that the numeric value of the physiological parameter falls within a normal range, and neglect whether or not the patient really feels a certain uncomfortable pathological symptom (such as dizziness, breathing difficulty and cold limbs, etc), and usually will result in missing the chance of an immediate treatment.

To overcome the aforementioned problems, some manufacturers build a status list containing several predetermined pathological symptoms in a physiological parameter detecting instrument, and the status list is provided for a patient to select the current physical conditions that the patient feels and transmits the status list to a healthcare center through the physiological parameter detecting instrument. Since a disease (such as heart disease) generally causes several pathological symptoms (such as heart throb, dizziness, breathing difficulty, cold limbs, chest pain, abnormal heart rhythm, and backache, etc), therefore there will be a large number of options or even pages in the status list. If a patient feels unwell, the patient needs to select a number of options listed in the status list and matched with the options that the patient feels. However, the patient is generally in a poor physical condition and emotionally tense, and thus it is difficult and inconvenient for the patient to concentrate on the selection from so many options. As a result, the time for returning the status list to the healthcare center will be delayed, and the patient cannot get help immediately or may even miss the prime time for an emergency treatment. Furthermore, different pathological symptoms incurred by a disease generally require different medicines or medical instruments or tools for the treatment. If a patient feels that there are so many options, the patient may hesitate to select the options or select a wrong option by mistake, and a medical professional may come to the site without appropriate medicines or medical tools. As a result, the rescue time may be delayed, and the patient's safety may be affected severely.

Therefore, it is an important subject for medical equipment manufacturers, hospitals and clinics to design a novel handling procedure and establish an appropriate number of options of pathological symptoms, so that patients can quickly select an option corresponding to the current physical condition that the patient feels, so as to reduce the time for medical professionals to know about the patient's self-perceived information and current physiological parameters, provide necessary medical assistance, prepare for appropriate medical tools, and improve the professionalism of the medical professionals.

SUMMARY OF THE INVENTION

In view of the aforementioned shortcomings of the conventional remote healthcare method, the inventor of the present invention based on years of experience in the related industry to conduct extensive researches and experiments, and finally designed a remote healthcare method for measuring a physiological parameter and reporting a self-perceived health status, in hope of overcoming the shortcomings of the prior art, and providing a quick and sufficient medical healthcare to patients.

Therefore, it is a primary objective of the present invention to provide a remote healthcare method for measuring a physiological parameter and reporting a self-perceived health status, and the remote healthcare method is applied to a healthcare server, wherein a self-perceived list is created according to a patient's medical history data and provided for a nursing professional to know about the patient's objective physiological parameters and subjective physical conditions, wherein the healthcare server includes a history database and a disease database, and the history database stores at least one patient's medical history datum having a unique patient identification code and an identification datum corresponding to the identification code and including at least one disease classification code. In addition, the disease database contains a plurality of diseases each having a unique disease classification code, and a plurality of pathological symptoms each corresponding to at least one physiological parameter. The healthcare server is connected to at least one physiological parameter detecting instrument through the Internet for transmitting data and information with each physiological parameter detecting instrument. The remote healthcare method implemented in the healthcare server comprises the steps of: reading a patient identification code and a physiological parameter from detected information after the healthcare server has received the detected information transmitted from the physiological parameter detecting instrument, and then reading an identification datum (such as a patient's name, age, address, telephone number, and emergency contact person, etc) matched with the patient identification code and a corresponding medical history datum from the history database according to a the read identification code, and reading a disease (such as a heart disease and a diabetes, etc) matched with the disease classification code and a corresponding pathological symptom (such as dizziness, heart throb, and breathing difficulty, etc) from the disease database according to at least one disease classification code (such as a heart disease code and a diabetes code, etc) contained in the medical history data, and then comparing the read physiological parameter with the pathological symptom corresponding to the physiological parameter, and screening a matched pathological symptom from the pathological symptoms to create a self-perceived list, and transmitting the self-perceived list to the physiological parameter detecting instrument for a patient to select a current matched pathological symptom, and waiting for a receipt of a self-perceived list returned from the physiological parameter detecting instrument, so that a medical professional can base on the content of the self-perceived list selected by the patient and the physiological parameter to determine an appropriate dosage of a medicine for the patient or bring an appropriate medical tool to the patient's place to improve the convenience of the medical professional's operation.

Another objective of the present invention is to review the physiological information and self-perceived list returned and reported by a patient each time for performing a statistical analysis to understand the frequency and type of the patient's illness when the patient sees a doctor or before a medical professional makes a diagnosis, so as to improve the accuracy of a medical professional's decision, and enhance the professionalism of the medical professional.

BRIEF DESCRIPTION OF THE DRAWINGS

FIG. 1 shows a schematic block diagram of a remote healthcare system in accordance with the present invention;

FIG. 2A shows a list of medical history data in accordance with the present invention;

FIG. 2B shows a list of diseases in accordance with the present invention;

FIG. 2C shows a self-perceived list in accordance with the present invention.

DETAILED DESCRIPTION OF THE PREFERRED EMBODIMENTS

Figure 3:
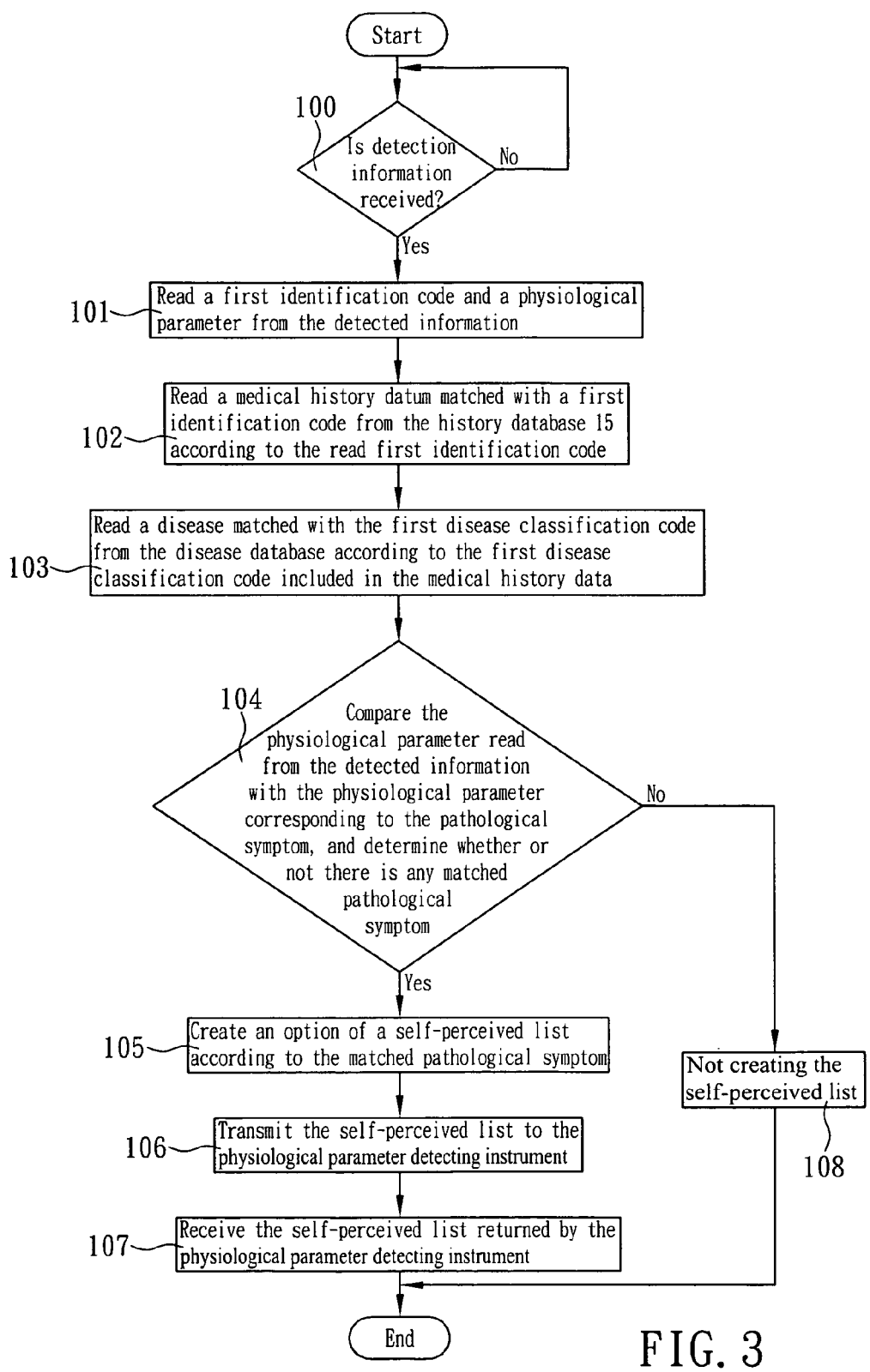
FIG. 3 is a flow chart of a remote healthcare method in accordance with a preferred embodiment of the present invention.

The present invention provides a remote healthcare method for measuring a physiological parameter and reporting a self-perceived health status, wherein a patient's objective information (including heartbeat rate, blood pressure, and body temperature, etc) and subjective information (including dizziness, heart throb, and breathing difficulty, etc) are returned to a healthcare center and provided for a medical professional to accurately determine a patient's current condition and immediately take necessary actions (such as informing the patient to take a certain medicine) for the patient, or carry a required medical tool or instrument to the patient's place, so as to improve the professionalism of the medical professional.

With reference to FIG. 1 for a remote healthcare method in accordance with a preferred embodiment of the present invention, the remote healthcare method is applied to a healthcare server 11 of a remote healthcare system 1, and the remote healthcare system 1 comprises the healthcare server 11 and at least one physiological parameter detecting instrument 13, and each physiological parameter detecting instrument 13 is connected to the healthcare server 11 via a cable connection (such as an ADSL or an optical fiber) or a wireless connection (such as WiFi, or 3.5G) through the Internet for transmitting/receiving data and information with the healthcare server 11, so that a medical professional can know about each patient's current physical condition from the healthcare server 11, and each physiological parameter detecting instrument 13 is installed in a specific position (such as a position adjacent to a patient bed or a dining room), or worn directly on a patient's body, for detecting the patient's physiological condition and obtaining the patient's current physiological parameter (including heartbeat rate, blood pressure, body temperature, and blood Glucose level, etc), and each physiological parameter detecting instrument 13 has a unique first identification code corresponding to a patient's identity, such that if the physiological parameter detecting instrument 13 has detected a patient's physical condition, the detected physiological parameter together with the first identification code will be converted into a detection signal to be transmitted to the healthcare server 11, and a medical professional can identify the patient having such physiological parameter by the first identification code.

With reference to FIGS. 1 and 2A, the healthcare server 11 includes a history database 15 and a disease database 17, and the history database 15 stores at least one patient's medical history data 151, and each medical history datum 151 includes a second identification code 1511 and an identification datum 1513 (such as a patient's name, age, address, telephone number, and emergency contact person, etc) corresponding to the second identification code 1511, wherein the second identification code 1511 is created according to the first identification code, and each medical history datum 151 further includes at least one first disease classification code 1515 (such as a heart disease code A, a kidney disease code B, a diabetes code C, and a chronic liver disease code D, etc), and the first disease classification code 1515 is classified according to a medical professional's diagnosis and set by a medical professional, and the quantity of first disease classification codes 1515 in each medical history datum 151 is created according to the diseases that the patient ever has. With reference to FIG. 2B, the disease database 17 stores a plurality of diseases 171 (such as heart disease; and diabetes, etc), and each disease 171 includes a unique second disease classification code 1711 and a unique disease name 1713, wherein the first disease classification code 1515 is created according to the second disease classification code 1711, and each disease 171 further includes a plurality of pathological symptoms 1715 (wherein the heart disease has pathological symptoms including dizziness, heart throb, chest pain, and breathing difficulty; and the kidney disease has pathological symptoms including edema, polyuria, and backache, etc), and each pathological symptom corresponds to at least one physiological parameter (such as heartbeat rate, blood pressure, and body temperature, etc), such that after the healthcare server 11 has received a detection signal transmitted from the physiological parameter detecting instrument 13, a first identification code and a physiological parameter will be read from the detected information, and an identification datum 1513 and a first disease classification code 1515 matched with the second identification code 1511 will be read from the history database 15 according to the read first identification code, and a disease name 1713 and a corresponding pathological symptom 1715 matched with the second disease classification code 1711 will be read from the disease database 17 according to the first disease classification code 1515 contained in the medical history data 151, and the healthcare server 11 will screen a pathological symptom from the corresponding pathological symptoms according to the read physiological parameter of the detected information to create a self-perceived list 111 (as shown in FIG. 2C). For example, if the numeric value of a physiological parameter such as a heartbeat rate and a breathing frequency of a patient's detected information is close to a numeric value of a physiological parameter corresponding to a pathological symptom 1715 of the heart disease such as dizziness, heart throb and breathing difficulty, the healthcare server 11 will create four options including "Dizziness", "Heart throb", "Breathing difficulty" and "None" in the self-perceived list 111. Since the options listed on the self-perceived list 111 are created according to the diseases that the patient ever has and the current physiological parameters of the patient, instead of all symptoms of a certain disease, therefore the number of option selected by the patient will be reduced significantly to make the patient's selection of options more convenient.

In FIGS. 1 to 2C, if the healthcare server 11 has received a detection signal from the physiological parameter detecting instrument 13 and produced a corresponding self-perceived list 111 according to the detection signal, then the self-perceived list 111 will be transmitted to the physiological parameter detecting instrument 13. Now, the patient can view the content of the self-perceived list 111 from a display screen of the physiological parameter detecting instrument 13, and select a matched pathological symptom according to the conditions that the patient feels, such that after the healthcare server 11 has received an option selected from the self-perceived list 111 and returned from the physiological parameter detecting instrument 13 again, the medical professional can determine a possible illness of the patient by the content of options selected by the patient and the patient's current physiological parameter and inform the patient about the handling method (such as taking a certain medicine) through the physiological parameter detecting instrument 13 or carry an appropriate medical instrument or tool to the patient's place.

To clearly disclose the aforementioned method, a processing flow of the healthcare server 11 is used as an example for illustrating the present invention as shown in FIGS. 1 to 3, and the method comprises the steps of:

(100) determining whether or not to receive detected information; if yes, go to Step (101), or else return to Step (100);

(101) reading a first identification code and a physiological parameter from the detected information, and then going to Step (102);

(102) reading a medical history datum 151 and a corresponding first disease classification code 1515 matched with the first identification code from the history database 15 according to the read first identification code, and then going to Step (103);

(103) reading a disease 171 matched with the first disease classification code 1515 from the disease database 17, a pathological symptom 1715 corresponding to the disease 171 and a physiological parameter corresponding to the pathological symptom 1715 according to the first disease classification code 1515 included in the medical history data 151, and then going to Step (104);

(104) comparing the physiological parameter read from the detected information with the physiological parameter corresponding to the pathological symptom 1715, and determining whether or not there is any matched pathological symptom 1715; if yes, go to Step (105), or else go to Step (108);

(105) creating an option of a self-perceived list 111 according to the matched pathological symptom 1715, and then going to Step (106);

(106) transmitting the self-perceived list 111 to the physiological parameter detecting instrument 13, and providing the self-perceived list 111 to a patient to view contents of the self-perceived list 111 from a display screen of the physiological parameter detecting instrument 13 and select an option matched with a pathological symptom according to the patient's current condition, and then going to Step (107) after the physiological parameter detecting instrument 13 has returned the pathological symptom selected by the patient to the healthcare server 11;

(107) receiving an option of the selected pathological symptom 1715 returned by the physiological parameter detecting instrument, and ending the procedure; and (108) not creating the self-perceived list 111, and then ending the procedure.

To illustrate the aforementioned technical characteristics of the invention, we use a patient who has a heart disease and a kidney disease as an example for illustrating the invention. In FIGS. 1 to 2C, if the patient feels unwell and presses a notice button on the physiological parameter detecting instrument 13, the physiological parameter detecting instrument 13 will detect the patient's physiological parameters and convert the patient's first identification code "001" and its physiological parameter into a detection signal, and transmit the detection signal to the healthcare server 11. After the healthcare server 11 has received the detection signal, the healthcare server 11 will read the first identification code "001" and its physiological parameter, and search a medical history datum 151 matched with the first identification code "001" from the history database 15. After a medical history datum 151 with a second identification code 1511 of "001", an identification datum 1513 (such as John, 30 years old, in Taipei city) and a first disease classification code 1515 (such as A or B) included in the medical history data 151 are found, the healthcare server 11 will search a disease 171 matched with the first disease classification code 1515 (such as A or B) from the disease database 17 according to the read first disease classification code 1515. After the diseases 171 having second disease classification codes 1711 of A and B are found, a disease name 1713 (such as heart disease and kidney disease), a pathological symptom 1715 included in each disease 171, and a physiological parameter corresponding to each pathological symptom 1715 of the disease 171 are read. Finally, the healthcare server 11 compares the physiological parameter in the detection signal with the physiological parameter corresponding to each pathological symptom 1715. If the patient's physiological parameter matches with a physiological parameter corresponding to the pathological symptom including "Dizziness", "Heart throb" and "Breathing difficulty" (or the numeric value of the physiological parameter equals to or falls within a range predetermined by a medical professional), then the healthcare server 11 will create a self-perceived list 111 and add four options including "Dizziness", "Heart throb", "Breathing difficulty" and "None" into the self-perceived list 111. The healthcare server 11 transmits the self-perceived list 111 to the patient's physiological parameter detecting instrument 13. Now, if the patient feels dizzy, then the patient selects the option of "dizziness", and the selected option is returned to the healthcare server 11, so that a medical professional can achieve a simple diagnosis by the patient's self-perceived condition and the physiological parameter, so as to determine the patient's current conditions immediately and inform the patient or the patient's nurse through the physiological parameter detecting instrument 13 or a telephone to take an appropriate medical treatment, so as to rescue the patient within the prime time, and the medical professional can prepare and bring an appropriate dosage of a medicine, an appropriate medical instrument, or tool to the patient's place immediately.

In FIG. 1, the options of the self-perceived list selected by the patient each time will be stored into the healthcare server 11 or the history database 15, such that if a patient feels unwell and goes to see a doctor, a medical professional can review the physiological information and self-perceived list returned by the patient each time for performing a statistical analysis before performing a diagnosis, so as to understand the frequency and type of the patient's unwell conditions, and improve the accuracy of the medical treatment, and enhance the professionalism of the medical professional for determining the patient's unwell conditions.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

In summation of the description above, the pathological symptoms listed in the self-perceived list of the present invention are compared with the patient's diseases in the medical history and the current physiological parameter, and the patient's most possible pathological symptoms are listed to save the patient's time of selecting the options, such that if the patient feels unwell, the patient can select the most appropriate option quickly to provide a convenient application to the patient, and medical professionals can know about the patient's current physiological parameter and self-perceived list from the healthcare server 11 to make a quick decision of the patient's condition and expedite the follow-up procedure.

While the invention has been described by means of specific embodiments, numerous modifications and variations could be made thereto by those skilled in the art without departing from the scope and spirit of the invention set forth in the claims.

What is claimed is:

1. A remote healthcare method for measuring a physiological parameter and reporting a self-perceived health status, which is applied to a healthcare server, comprising the steps of:
    reading a patient identification code and a physiological parameter contained in the detected information, after receiving detected information transmitted from a physiological parameter detecting instrument;
    reading identification data and medical history data matched with the patient identification code from a history database according to the patient identification code;
    reading a disease and a corresponding pathological symptom matched with the disease classification code from the disease database according to at least one disease classification code contained in the medical history data;
    selecting an option matched with the pathological symptom from the corresponding pathological symptoms to create a self-perceived list according to the physiological parameter read from the detected information, and transmitting the self-perceived list to the physiological parameter detecting instrument; and
    receiving the option selected by a patient and transmitted from the physiological parameter detecting instrument.

2. The remote healthcare method of claim 1, wherein the healthcare server includes the history database, and the history database stores at least one patient's medical history data, and each medical history datum includes a corresponding patient identification code and an identification datum corresponding to the identification code, and includes at least one disease classification code.

3. The remote healthcare method of claim 2, wherein the physiological parameter detecting instrument having a corresponding patient identification code is connected to the healthcare server through the Internet for transmitting data and information with the healthcare server and the remote healthcare method further includes a procedure carried out by the physiological parameter detecting instrument and comprising the steps of:
    detecting a patient's current physiological parameter;
    converting a corresponding patient identification code in the physiological parameter detecting instrument and the detected physiological parameter into detected information; and
    transmitting the detected information to the healthcare server.

4. The remote healthcare method of claim 3, wherein the healthcare server will not create the self-perceived list when the healthcare server screens no matched pathological symptom.

5. The remote healthcare method of claim 4, wherein the quantity of disease classification codes in the medical history data is set according to the diseases that a patient with the corresponding patient identification data ever has.

6. The remote healthcare method of claim 5, wherein the option selected by a patient is returned and stored into the healthcare server.

7. The remote healthcare method of claim 5, wherein the option selected by a patient is returned and stored into the history database.

8. The remote healthcare method of claim 5, wherein the physiological parameter detecting instrument transmits detected information to a healthcare server via a wireless transmission method.

9. The remote healthcare method of claim 1, wherein the healthcare server includes the disease database, and the disease database stores a plurality of diseases, each having a unique disease classification code, and includes a plurality of pathological symptoms, each corresponding to at least one physiological parameter.

10. The remote healthcare method of claim 9, wherein the physiological parameter detecting instrument having a corresponding patient identification code is connected to the healthcare server through the Internet for transmitting data and information with the healthcare server, and the remote healthcare method further includes a procedure carried out by the physiological parameter detecting instrument and comprising the steps of:
- detecting a patient's current physiological parameter;
- converting a corresponding patient identification code in the physiological parameter detecting instrument and the detected physiological parameter into detected information; and
- transmitting the detected information to the healthcare server.

11. The remote healthcare method of claim 10, the healthcare server will create a self-perceived list when the healthcare server screens no matched pathological symptom.

12. The remote healthcare method of claim 11, wherein the quantity of disease classification codes in the medical history data is set according to the diseases that a patient with the corresponding patient identification data ever has.

13. The remote healthcare method of claim 12, wherein the option selected by a patient is returned and stored into the healthcare server.

14. The remote healthcare method of claim 12, wherein the option selected by a patient is returned and stored into the history database.

15. The remote healthcare method of claim 1, wherein the physiological parameter detecting instrument having a corresponding patient identification code is connected to the healthcare server through the Internet for transmitting or receiving data and information with the healthcare server, and the remote healthcare method further includes a procedure carried out by the physiological parameter detecting instrument and comprising the steps of:
- detecting a patient's current physiological parameter;
- converting a corresponding identification code in the physiological parameter detecting instrument and the detected physiological parameter into detected information; and
- transmitting the detected information to the healthcare server.

16. The remote healthcare method of claim 15, wherein the healthcare server will not create the self-perceived list when the healthcare server screens no matched pathological symptom.

17. The remote healthcare method of claim 16, wherein the quantity of disease classification codes in the medical history data is set according to the diseases that a patient with the corresponding patient identification data ever has.

18. The remote healthcare method of claim 17, wherein the option selected by a patient is returned and stored in the healthcare server.

19. The remote healthcare method of claim 17, wherein the option selected by a patient is returned and stored into the history database.

20. The remote healthcare method of claim 17, wherein the physiological parameter detecting instrument transmits detected information to a healthcare server via a wireless transmission method.

* * * * *